(12) United States Patent
Rizzi et al.

(10) Patent No.: US 7,820,698 B2
(45) Date of Patent: Oct. 26, 2010

(54) PHOSPHODIESTERASE-4 INHIBITORS BELONGING TO THE TERTIARY AMINE CLASS

(75) Inventors: Andrea Rizzi, Parma (IT); Elisabetta Armani, Parma (IT); Ilaria Peretto, Parma (IT); Elena La Porta, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 12/423,227

(22) Filed: Apr. 14, 2009

(65) Prior Publication Data

US 2009/0258905 A1  Oct. 15, 2009

(30) Foreign Application Priority Data

Apr. 14, 2008  (EP) .................................. 08007284

(51) Int. Cl.
- *A61K 31/44* (2006.01)
- *C07D 213/24* (2006.01)
- *C07D 405/00* (2006.01)
- *C07D 409/00* (2006.01)

(52) U.S. Cl. ........................ 514/336; 514/357; 546/334; 546/283.4; 546/280.4

(58) Field of Classification Search .................. 546/334, 546/283.4, 280.4; 514/357
See application file for complete search history.

(56) References Cited

FOREIGN PATENT DOCUMENTS

| WO | 02/074726 | 9/2002 |
|---|---|---|
| WO | 2004/009552 | 1/2004 |
| WO | 2005/061458 | 7/2005 |
| WO | 2006/135828 | 12/2006 |
| WO | 2008/006509 | 1/2008 |

*Primary Examiner*—Janet L Andres
*Assistant Examiner*—Binta M Robinson
(74) *Attorney, Agent, or Firm*—Oblon, Spivak, McClelland, Maier & Neustadt, L.L.P.

(57) ABSTRACT

Compounds of formula (I):

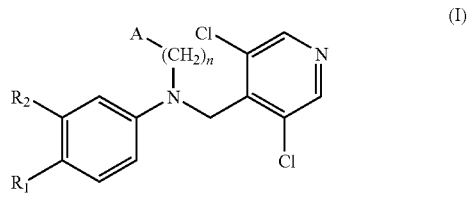

wherein n, A, $R_1$, and $R_2$ are defined in the specification, are useful as inhibitors of the phosphodiesterase 4 (PDE4) enzyme and for treating certain conditions.

24 Claims, No Drawings

PHOSPHODIESTERASE-4 INHIBITORS BELONGING TO THE TERTIARY AMINE CLASS

CROSS REFERENCES TO RELATED APPLICATIONS

This application claims priority to European Patent Application No. 08007284.6 filed on Apr. 14, 2008, which is incorporated herein by reference in its entirety.

BACKGROUND OF THE INVENTION

1. Field of the Invention

The present invention relates to inhibitors of the phosphodiesterase 4 (PDE4) enzyme. The present invention further relates to methods of preparing such inhibitors, compositions which contain such an inhibitor, and methods of treating and/or preventing certain diseases by administering an effective amount of such an inhibitor.

2. Discussion of the Background

The cyclic nucleotide specific phosphodiesterases (PDEs) comprise a family with eleven isoenzymes, known at present, that catalyze the hydrolysis of various cyclic nucleoside monophosphates (including cAMP and cGMP). These cyclic nucleotides act as second messengers within cells and as messengers, carry impulses from cell surface receptors having bound various hormones and neurotransmitters. PDEs regulate the level of cyclic nucleotides within cells and maintain cyclic nucleotide homeostasis by degrading such cyclic mononucleotides resulting in termination of their messenger role.

The isoenzymes can be grouped according to their specificity toward hydrolysis of cAMP or cGMP, their sensitivity to regulation by calcium, calmodulin or cGMP, and their selective inhibition by various compounds.

PDE4 is cAMP specific and its inhibition causes airway relaxation, anti-inflammatory, enhanced cognition, and anti-depressant activity.

Therefore inhibitors of PDE4 isoenzymes are therapeutic agents which may be useful in treating diseases involving inflammation, such as asthma or arthritis, or diseases of the central nervous such as cognitive decline or memory loss.

Various chemical classes of PDE4 inhibitors are known.

In particular, PDE4 inhibitors belonging to the tertiary amine class have been described in WO 2005/061458 and WO 2006/135828.

However, it is generally known that compounds having $IC_{50}$ values higher that 1000 nM may show an unsatisfactory therapeutic activity.

As a consequence, the activity of the known PDE4 inhibitors, in particular of those belonging to the tertiary amine class, still requires improvement.

Thus, there remains a need for compounds belonging to the tertiary amine class, whose activity is improved compared to the known PDE4 inhibitors.

SUMMARY OF THE INVENTION

Accordingly, it is one object of the present invention to provide novel PDE4 inhibitors.

It is another object of the present invention to provide novel PDE4 inhibitors belonging to the tertiary amine class with improved activity.

It is another object of the present invention to provide novel methods of preparing such an inhibitor.

It is another object of the present invention to provide novel pharmaceutical compositions which contain such an inhibitor.

It is another object of the present invention to provide novel methods of treating and/or preventing certain diseases by administering an effective amount of such an inhibitor.

These and other objects, which will become apparent during the following detailed description, have been achieved by the inventors' discovery that tertiary amine derivatives of general formula (I)

(I)

wherein:

n=1 or 2, preferably 1

$R_1$ and $R_2$ are different or the same and are independently selected from the group consisting of $C_1$-$C_4$ alkyloxy;

$C_3$-$C_7$ cycloalkyloxy; and ($C_3$-$C_7$)-cycloalkyl-($C_1$-$C_3$)-alkyloxy;

and wherein at least one of $R_1$ and $R_2$ is $C_1$-$C_4$ alkyloxy;

A is an unsaturated ring system, that is a mono- or bicyclic ring such as aryl or heteroaryl, having 5 to 10 ring atoms in which at least one ring atom is a heteroatom (e.g. N, S or O), and which is optionally substituted by one or more substituents independently selected from the group consisting of:

$C_1$-$C_6$ alkyl optionally substituted by one or more $C_3$-$C_7$ cycloalkyl;

$C_2$-$C_6$ alkenyl optionally substituted by one or more $C_3$-$C_7$ cycloalkyl;

$C_2$-$C_6$ alkynyl optionally substituted by one or more $C_3$-$C_7$ cycloalkyl;

$C_3$-$C_7$ cycloalkyl;

$C_5$-$C_7$ cycloalkenyl;

$C_3$-$C_7$ cycloalkyloxy;

$OR_3$ wherein $R_3$ is selected from the group consisting of

H;

$C_1$-$C_6$ alkyl optionally substituted by one or more $C_3$-$C_7$ cycloalkyl;

$C_3$-$C_7$ cycloalkyl;

phenyl;

benzyl; and $NR_4R_5$—$C_1$-$C_4$ alkyl wherein $R_4$ and $R_5$ are each independently H or $C_1$-$C_6$ alkyl or they form with the nitrogen atom to which they are linked a saturated or partially saturated ring, preferably a piperidyl ring;

halogen atoms;

CN;

$NO_2$;

$NR_6R_7$ wherein $R_6$ and $R_7$ are different or the same and are independently selected from the group consisting of

H;

$C_1$-$C_6$ alkyl, optionally substituted with phenyl;

$C_1$-$C_4$ alkylsulfonyl;
$COC_6H_5$; and
$COC_1$-$C_4$ alkyl;
or they form with the nitrogen atom to which they are linked a saturated or partially saturated ring, preferably a piperidyl ring;
$COR_8$ wherein $R_8$ is OH, $NH_2$, phenyl or $C_1$-$C_6$ alkyl;
oxo;
$HNSO_2R_9$ wherein $R_9$ is $C_1$-$C_4$ alkyl or a phenyl optionally substituted with halogen atoms or with a $C_1$-$C_4$ alkyl group;
$SO_2R_{10}$ wherein $R_{10}$ is $C_1$-$C_4$ alkyl, OH or $NR_6R_7$ wherein $R_6$ and $R_7$ are as defined above;
$SOR_{11}$ wherein $R_{11}$ is phenyl or $C_1$-$C_4$ alkyl;
$SR_{12}$ wherein $R_{12}$ is H, phenyl or $C_1$-$C_4$ alkyl;
$COOR_{13}$ wherein $R_{13}$ is H, $C_1$-$C_4$ alkyl, phenyl, benzyl and $(CH_2)_qOR_{14}$, wherein q=1, 2, 3 or 4 and $R_{14}$ is H, $C_1$-$C_4$ alkyl or $C_1$-$C_4$ cycloalkyl and pharmaceutically acceptable salts thereof,
are effective as PDE4 inhibitors.

The present invention also provides pharmaceutical compositions of compounds of general formula (I) alone or in combination with one or more pharmaceutically acceptable carriers.

In a further aspect the present invention provides the use of compounds of general formula (I) for the preparation of a medicament for the prevention and/or treatment of any disease wherein PDE4 inhibition is required.

The present invention also provides the use of compounds of general formula (I) for preparing a medicament.

In a further aspect, the present invention provides the use of compounds of general formula (I) for the preparation of a medicament for the prevention and/or treatment of an inflammatory disease, disorder or condition characterized by or associated with an undesirable inflammatory immune response or induced by or associated with an excessive secretion of TNF-α and PDE4.

The present invention also provides compounds for use in the treatment of neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury. Moreover the present invention provides a method for prevention and/or treatment of an inflammatory disease, disorder or condition characterized by or associated with an undesirable inflammatory immune response or induced by or associated with an excessive secretion of TNF-α and PDE4 which comprises administering to a subject in need thereof a therapeutically effective amount of a compound of general formula (I).

DESCRIPTION OF THE PREFERRED EMBODIMENTS

The term "halogen atoms" as used herein includes fluorine, chlorine, bromine, and iodine, preferably chlorine.

As used herein, the expression "linear or branched $C_1$-$C_x$ alkyl" where x is an integer greater than 1, refers to straight-chained and branched alkyl groups wherein the number of constituent carbon atoms is in the range 1 to x. Particular alkyl groups are methyl, ethyl, n-propyl, isopropyl, and t-butyl.

Optionally one or more hydrogen atoms in said groups can be replaced by halogen atoms, preferably chlorine or fluorine.

The derived expressions "$C_2$-$C_6$ alkenyl" and "$C_2$-$C_6$ alkynyl", are to be construed in an analogous manner.

As used herein, the expression "$C_3$-$C_x$ cycloalkyl", where x is an integer greater than 3, refers to cyclic non-aromatic hydrocarbon groups containing from 3 to x ring carbon atoms. Examples include cyclopropyl, cyclobutyl, cyclopentyl, cyclohexyl, and cycloheptyl.

Optionally one or more hydrogen atoms in said groups can be replaced by halogen atoms, preferably chlorine or fluorine.

The derived expression "$C_5$-$C_x$ cycloalkenyl", where x is an integer greater than 5, is to be construed in an analogous manner.

As used herein, the expression "ring system" refers to mono- or bicyclic ring systems which may be saturated, partially unsaturated or unsaturated, such as aryl, $C_3$-$C_8$ cycloalkyl or heteroaryl, having 5 to 10 ring atoms in which at least one ring atom is a hereoatom (e.g. N, S, or O).

Examples of suitable monocyclic systems include thiophene, phenyl, and furan. Examples of suitable bicyclic systems include naphthyl and benzothiophene.

Compounds belonging to the tertiary amine class in which the substituents are an aromatic ring substituted with two alkyloxy groups, an arylmethyl group and a pyridinilmethyl group have been synthesized.

The present invention provides tertiary amines derivatives of general formula (I)

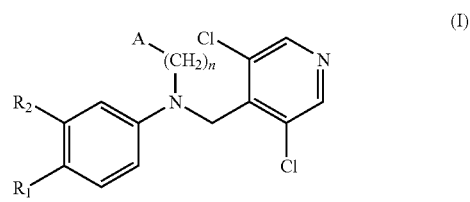

(I)

Pharmaceutically acceptable salts include those obtained by reacting the compound with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid.

Pharmaceutically acceptable salts also include those in which acidic functions, when present, are reacted with an appropriate base to form, e.g., sodium, potassium, calcium, magnesium, ammonium, and chloride salts.

It has been found that when the phenyl group in A is replaced by the cycloalkyl moiety, the activity falls, in particular in the cell-based assay.

Moreover, from the analysis of the screening results it emerges that hydrogen bond donor or acceptor substituents on the phenyl ring in the A region seem to be preferred, in fact they give rise to compounds showing an improved inhibitory activity in the cell-free assay.

It also been found that compounds in which A is directly linked to the amino nitrogen show an activity higher than 1000 nM in the $IC_{50}$ PBMCs assay.

In one of the preferred embodiments, $R_1$ and $R_2$ are $C_1$-$C_4$ alkyloxy.

In a particular embodiment of the invention, A is a heteroaryl ring selected from the group consisting of furan or benzothiophene.

In another particular embodiment of the invention, A is naphthyl.

In one of the preferred embodiments of the invention, A is phenyl.

In one of the preferred embodiment, the optional substituent Rx of the ring system A is selected from the group consisting of $C_1$-$C_6$ alkyl, halogen atom, preferably fluorine; $SO_2R_{10}$ wherein $R_{10}$ is $C_1$-$C_4$ alkyl, preferably methyl or $NH_2$; CN; OH; $COR_8$ wherein Rx is preferably OH; $HNSO_2R_9$ wherein $R_9$ is $C_1$-$C_4$ alkyl, preferably methyl.

In one of the preferred embodiments of the present invention, Rx is a hydrogen bond donor or acceptor substituent selected from the group consisting of $OR_3$ wherein $R_3$ is $C_1$-$C_6$ alkyl, preferably methyl or $NR_6R_7$.

According to a preferred embodiment, the present invention provides the following compounds:

| Compound | Chemical name |
|---|---|
| C1 | (3,5-Dichloro-pyridin-4-ylmethyl)-(3,4-dimethoxy-phenyl)-(4-fluoro-benzyl)-amine |
| C2 | 3-{[(3,5-Dichloro-pyridin-4-ylmethyl)-(3,4-dimethoxy-phenyl)-amino]-methyl}-benzonitrile |
| C3 | (3,5-Dichloro-pyridin-4-ylmethyl)-(3,4-dimethoxy-phenyl)-(3-methoxy-benzyl)-amine |
| C4 | (3,5-Dichloro-pyridin-4-ylmethyl)-(3,4-dimethoxy-phenyl)-(4-methanesulfonyl-benzyl)-amine |
| C5 | Benzyl-(3,5-dichloro-pyridin-4-ylmethyl)-(3,4-dimethoxy-phenyl)-amine |
| C6 | (3,5-Dichloro-pyridin-4-ylmethyl)-(3,4-dimethoxy-phenyl)-phenethyl-amine |
| C7 | (3,5-Dichloro-pyridin-4-ylmethyl)-(3,4-dimethoxy-benzyl)-(3,4-dimethoxy-phenyl)-amine |
| C8 | (3,5-Dichloro-pyridin-4-ylmethyl)-(3,4-dimethoxy-phenyl)-(3-fluoro-4-methoxy-benzyl)-amine |
| C9 | (3,5-Dichloro-pyridin-4-ylmethyl)-(3,4-dimethoxy-phenyl)-furan-2-ylmethyl-amine |
| C10 | 4-{[(3,5-Dichloro-pyridin-4-ylmethyl)-(3,4-dimethoxy-phenyl)-amino]-methyl}-benzenesulfonamide |
| C11 | 4-{[(3,5-Dichloro-pyridin-4-ylmethyl)-(3,4-dimethoxy-phenyl)-amino]-methyl-benzoic acid methyl ester |
| C12 | N-(3-{[(3,5-Dichloro-pyridin-4-ylmethyl)-(3,4-dimethoxy-phenyl)-amino]-methyl-phenyl)-methanesulfonamide |
| C13 | (3,5-Dichloro-pyridin-4-ylmethyl)-(3,4-dimethoxy-phenyl)-(4-methoxy-benzyl)-amine |
| C14 | (3,5-Dichloro-pyridin-4-ylmethyl)-(3-ethoxy-4-methoxy-phenyl)-(4-methoxy-benzyl)-amine |
| C15 | (3,5-Dichloro-pyridin-4-ylmethyl)-(3-isopropoxy-4-methoxy-phenyl)-(4-methoxy-benzyl)-amine |
| C16 | 4-{[(3,5-dichloro-pyridin-4-ylmethyl)-(3,4-dimethoxy-phenyl)-amino]-methyl}-benzoic acid |
| C17 | (3,5-Dichloro-pyridin-4-ylmethyl)-(3,4-dimethoxy-phenyl)-thiophen-2-ylmethyl-amine |
| C18 | Benzo[b]thiophen-2-ylmethyl-(3,5-dichloro-pyridin-4-ylmethyl)-(3,4-dimethoxy-phenyl)-amine |
| C19 | 3-{[(3,5-Dichloro-pyridin-4-ylmethyl)-(3,4-dimethoxy-phenyl)-amino]-methyl-phenol |

The compounds of general formula (I) may be prepared according to conventional methods. Examples of the processes which can be used are described below and reported in Scheme I shown below.

Scheme I

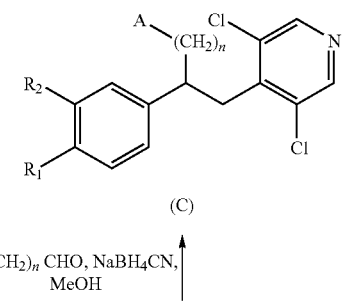

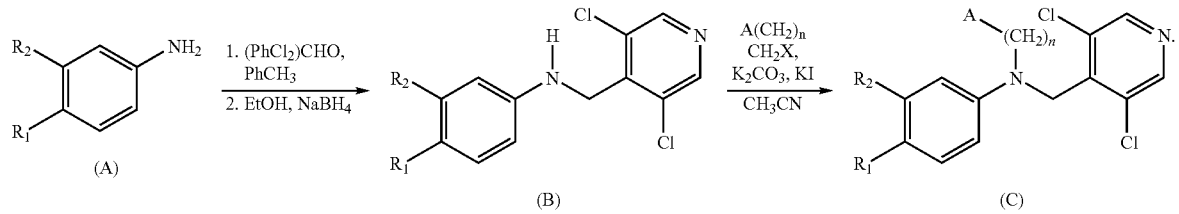

As reported in Scheme I, the compounds of general formula (I) are prepared according to a process which includes the following steps, the procedure for the preparation of amine of formula (A) being well known:

1$^{st}$ step—functionalization of an amine of formula (A) by reductive amination with an appropriate aldehyde (PhCl$_2$)—CHO to give a secondary amine of general formula (B). The reaction may be carried out for example by formation of the imine intermediate in toluene with molecular sieves, followed by evaporation of the solvent and subsequent reduction of the imine derivative with sodium boron hydride (NaBH$_4$) in ethanol.

2$^{nd}$ step—further functionalization of the secondary amine of general formula (B), by means of either reductive amination or alkylation with primary alkylating agents to give final compounds of general formula (C).

The present invention also provides pharmaceutical compositions of compounds of general formula (I) in admixture with one or more pharmaceutically acceptable carriers, for example those described in Remington's Pharmaceutical Sciences Handbook, XVII Ed., Mack Pub., N.Y., U.S.A.

Administration of the compounds of the present invention may be accomplished according to patient's needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including but not limited to suspending agents, solubilizers, buffering agents, binders, disintegrants, preservatives, colorants, flavours, lubricants and the like. Time release capsules, tablets and gels are also advantageous.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavours, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, suitable known carriers.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound. Advantageously, the compounds of general formula (I) can be administered for example, at a dosage comprised between 0.001 and 1000 mg/day, preferably between 0.1 and 500 mg/day.

The compounds of general formula (I) may be administered for the prevention and/or treatment of any disease wherein PDE4 inhibition is required. Said disease include: diseases involving inflammation such as asthma and COPD, allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritis in the anogenital area, alopecia greata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Example 1

Preparation of Intermediates (a) (Scheme)

Preparation of (3-ethoxy-4-methoxy-phenyl)-amine (A2)

Step 1: preparation of 2-ethoxy-1-methoxy-4-nitro-benzene 2-methoxy-5-nitro-phenol (508 mg, 3 mmoles) was dissolved in DMF (20 mL) under nitrogen atmosphere. K$_2$CO$_3$ (900 mg, 6.5 mmoles), KI (490 mg, 2.95 mmol) and ethyl bromide (0.250 mL, 3.3 mmoles) were added, and the suspension was heated to 40° C. for 28 hours. The mixture was diluted with AcOEt (60 mL) and extracted with 1N NaOH (40 mL) and water (40 mL). The organic layer was dried over Na$_2$SO$_4$ and evaporated to dryness. The crude was employed in the next step without purification.

Step 2: preparation of 3-ethoxy-4-methoxy-aniline

The crude material obtained in Step 1 was dissolved in ethanol (99%, 20 mL). Pd/C (10%, 60 mg) and ammonium formate (1.71 g) were added, and the resulting mixture was stirred at room temperature for 1 hour. The catalyst was removed by filtration and the solvent was evaporated under reduced pressure. The crude was purified by flash chromatography (SiO$_2$, petroleum ether/AcOEt from 7/3 to 5/5). The title compound was obtained in amount of 325 mg. The same procedure was applied for the synthesis of (A2) (3-isopropoxy-4-methoxy-phenyl)-amine), using suitable reagents.

TABLE 1

Compound

R2—⟨phenyl⟩—NH2
R1

| Compound | $R_1$ | $R_2$ | Analytical characterization |
|---|---|---|---|
| (A1) | OMe | OEt | MS(ESI$^+$): 168.1 (MH$^+$) |
| (A2) | OMe | OPr | MS(ESI$^+$): 182.2 (MH$^+$) |

Example 2

Preparation of Intermediates (B) (Scheme)

Preparation of (3,5-Dichloro-pyridin-4-ylmethyl)-(3,4-dimethoxy-phenyl)-amine (B1)

Commercially available 3,4-dimethoxy-phenyl-amine (1.74 g, 11.3 mmoles) and 3,5-dichloro-pyridine-4-carbaldehyde (2.0 g, 11.3 mmoles) were dissolved in toluene (40 mL) under nitrogen atmosphere. Molecular sieves (4A, 1 g) were added, and the mixture was heated to reflux. Reaction monitoring was performed by TLC analysis (petroleum ether/AcOEt 7/3): formation of the imine intermediate was completed after 3 hours. Molecular sieves were removed by filtration and the solvent was evaporated. The residue was dissolved in ethanol (99%, 40 mL). The solution was cooled to 0° C. and NaBH$_4$ (559 mg, 14.7 mmol) was added. The resulting mixture was stirred at room temperature for 18 hours, then water was added (50 mL), and the mixture was extracted AcOEt (3×60 mL). The organic layer was washed with brine, dried over Na$_2$SO$_4$ and evaporated to dryness. The crude was purified by flash chromatography (SiO$_2$, petroleum ether/AcOEt from 9/1 to 7/3). The title compound was obtained as a yellow solid (3.04 g).

The following compounds were prepared following the same synthetic procedure, using suitable reagents:

TABLE 2

Compound

| Compound | $R_1$ | $R_2$ | Analytical characterization |
|---|---|---|---|
| (B1) | OMe | OMe | MS(ESI$^+$): 313.0 (MH$^+$) |
| (B2) | OMe | OEt | MS(ESI$^+$): 327.1 (MH$^+$) |
| (B3) | OMe | OPr | MS(ESI$^+$): 341.1 (MH$^+$) |

Example 3

Preparation of Compounds (C) (Scheme)

Preparation of (3,5-dichloro-pyridin-4-ylmethyl)-(3,4-dimethoxy-phenyl)-(4-fluoro-benzyl)-amine (C1)

Intermediate B1 (480 mg, 1.5 mmoles) was dissolved in CH$_3$CN (7.5 mL). Solid K$_2$CO$_3$ (518 mg, 3.75 mmoles), solid KI (250 mg, 1.5 mmoles) and neat 4-fluoro-benzyl-bromide (0.191 mL, 1.5 mmoles) were added, and the mixture was heated in a sealed vial in a microwave oven at 120° C. for 30+30 minutes. The reaction mixture was diluted with water (40 mL) and extracted with AcOEt (3×40 mL). The organic layer was washed with brine, dried over Na$_2$SO$_4$, and evaporated to dryness. The crude was purified by flash chromatography (SiO$_2$, petroleum ether/AcOEt from 9/1 to 7/3). The title compound was obtained as a light-yellow solid in amount of 407 mg.

The final compounds listed below and reported in Table 3 were prepared according to the same procedure, employing either intermediate B I or B2, B3, B4 and the appropriate alkylating agents. In Table 3, the symbol * in the formulae for the group A indicates the position at which the group A is bonded to the remainder of the molecule.

TABLE 3

| Compound | $R_1$ | $R_2$ | $(CH_2)_n$ | A | Analytical characterization |
|---|---|---|---|---|---|
| C1 | OMe | OMe | n = 1 | *-C$_6$H$_4$-F | MS (ESI$^+$) 420.9 (MH$^+$) ($^1$H-NMR CDCl$_3$): 8.40 (s, 2 H); 7.15(dd, 2 H); 6.88(dd, 2 H); 6.73(d, 1 H); 6.52-6.47(m, 2 H); 4.58(s, 2 H); 4.30(s, 2 H); 3.80(s, 3 H); 3.74(s, 3 H) |
| C2 | OMe | OMe | n = 1 | *-C$_6$H$_4$-CN | MS (ESI$^+$) 428.0 (MH$^+$) ($^1$H-NMR CDCl$_3$): 8.41 (s, 2 H); 7.52(s, 1 H); 7.44(m, 2 H); 7.30(dd, 1 H); 6.73(d, 1 H); 6.50(m, 2 H); 4.60(s, 2 H); 4.34(s, 2 H); 3.81(s, 3 H); 3.76(s, 3 H) |

TABLE 3-continued

| Compound | R₁ | R₂ | (CH₂)ₙ | A | Analytical characterization |
|---|---|---|---|---|---|
| C3 | OMe | OMe | n = 1 | 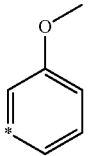 | MS (ESI⁺) 433.1 (MH⁺) (¹H-NMR CDCl₃): 8.40 (s, 2 H); 7.12(dd, 1 H); 6.82-6.66(m, 4 H); 6.57-6.49(m, 2 H); 4.64(s, 2 H); 4.35(s, 2 H); 3.80(s, 3 H); 3.74(s, 3 H); 3.73(s, 3 H) |
| C4 | OMe | OMe | n = 1 | 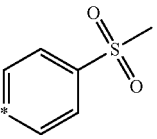 | MS (ESI⁺) 481.1 (MH⁺) (¹H-NMR CDCl₃): 8.41 (s, 2 H); 7.77(d, 2 H); 7.42(d, 2 H); 6.72(d, 1 H); 6.57(d, 1 H); 6.50(dd, 1 H); 4.64(s, 2 H); 4.43(s, 2 H); 3.81(s, 3 H); 3.76(s, 3 H); 2.99(s, 3 H) |
| C5 | OMe | OMe | n = 1 |  | MS (ESI⁺) 403.1 (MH⁺) (¹H-NMR CDCl₃): 8.40 (s, 2 H); 7.27-7.10(m, 5 H); 6.73(d, 1 H); 6.54(d, 1 H); 6.52(dd, 1 H); 4.64(s, 2 H); 4.38(s, 2 H); 3.80(s, 3 H); 3.73(s, 3 H) |
| C6 | OMe | OMe | n = 2 |  | MS (ESI⁺) 417.1 (MH⁺) (¹H-NMR CDCl₃): 8.44 (s, 2 H); 7.29-7.14(m, 3 H); 7.08(m, 2 H); 6.81(d, 1 H); 6.55(d, 1 H); 6.53(dd, 1 H); 4.51(s, 2 H); 3.85(s, 3 H); 3.84(s, 3 H); 3.38(dd, 2 H); 2.76(dd, 2 H) |
| C7 | OMe | OMe | n = 1 | 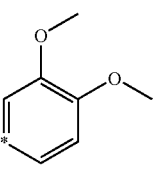 | MS (ESI⁺) 462.1 (MH⁺) (1H-NMR CDCl3): 7.26 (s, 2 H); 6.81-6.67(m, 4 H); 6.60-6.51(m, 2 H); 4.61(s, 2 H); 4.30(s, 2 H); 3.82(s, 3 H); 3.81(s, 3 H); 3.79(s, 3 H); 3.75(s, 3 H) |
| C8 | OMe | OMe | n = 1 | 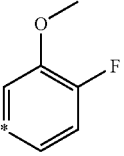 | MS (ESI⁺) 451.1 (MH⁺) (¹H-NMR CDCl₃): 8.41 (s, 2 H); 6.93-6.81(m, 2 H); 6.94(d, 1 H); 6.69(m, 1 H); 6.53(m, 2 H); 4.60(s, 2 H); 4.28(s, 2 H); 3.81(s, 3 H); 3.79(s, 3 H); 3.75(s, 3 H) |
| C9 | OMe | OMe | n = 1 |  | MS (ESI⁺) 392.1 (MH⁺) (1H-NMR CDCl3): 8.42 (s, 2 H); 7.29(dd, 1 H); 6.74(d, 1 H); 6.55(d, 1 H); 6.53(dd, 1 H); 6.23(dd, 1 H); 6.06(dd, 1 H); 4.61(s, 2 H); 4.32(s, 2 H); 3.81(s, 3 H); 3.79(s, 3 H) |
| C10 | OMe | OMe | n = 1 | 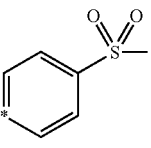 | MS (ESI⁺) 482.1 (MH⁺) (¹H-NMR CDCl₃): 8.40 (s, 2 H); 7.75(d, 2 H); 7.36(d, 2 H); 6.72(d, 1 H); 6.75(d, 1 H); 6.49(dd, 1 H); 4.71(s, br, 2 H); 4.63(s, 2 H); 4.40(s, 2 H); 3.81(s, 3 H); 3.76(s, 3 H) |

TABLE 3-continued

| Compound | $R_1$ | $R_2$ | $(CH_2)_n$ | A | Analytical characterization |
|---|---|---|---|---|---|
| C11 | OMe | OMe | n = 1 | *-C6H4-C(=O)-OMe (methyl benzoate) | MS (ESI$^+$) 461.2 (MH$^+$) ($^1$H-NMR CDCl$_3$): 8.40 (s, 2 H); 7.87(d, 2 H); 7.27(d, 2 H); 6.72(d, 1 H); 6.51(d, 1 H); 6.49(dd, 1 H); 4.63(s, 2 H); 4.39(s, 2 H); 3.88(s, 3 H); 3.80(s, 3 H); 3.74(s, 3 H) |
| C12 | OMe | OMe | n = 1 | *-C6H4-NH-S(=O)2-Me | MS (ESI$^+$) 496.2 (MH$^+$) ($^1$H-NMR CDCl$_3$): 8.43 (s, 2 H), 6.95-7.24(m, 4 H), 6.72(d, 1 H), 6.63(d, 1 H), 6.56(dd, 1 H), 6.43 (br.s., 1 H), 4.68(s, 2 H), 4.40(s, 2 H), 3.80(s, 3 H), 3.75(s, 3 H), 2.89(s, 3 H) |
| C13 | OMe | OMe | n = 1 | *-C6H4-OMe | MS (ESI$^+$) 433.1 (MH$^+$) ($^1$H-NMR CDCl$_3$): 8.39 (s, 2 H); 7.10(d, 2 H); 6.73(m, 3 H); 6.50(m, 2 H); 4.58(s, 2 H); 4.29(s, 2 H); 3.80(s, 3 H); 3.75(s, 3 H); 3.74(s, 3 H) |
| C14 | OMe | OEt | n = 1 | *-C6H4-OMe | MS (ESI$^+$) 447.1 (MH$^+$) ($^1$H-NMR CDCl$_3$): 8.41 (s, 2 H), 7.11(m, 2 H), 6.68-6.88(m, 3 H), 6.43-6.62 (m, 2 H), 4.59(s, 2 H), 4.29(s, 2 H), 3.98(q, 2 H), 3.81(s, 3 H), 3.77(s, 3 H), 1.39(t, 3 H) |
| C15 | OMe | OPr | n = 1 | *-C6H4-OMe | MS (ESI$^+$) 461.0 (MH$^+$) ($^1$H-NMR CDCl$_3$): 8.40 (s, 2 H), 7.10(m, 2 H), 6.68-6.80(m, 3 H), 6.47-6.62 (m, 2 H), 4.58(s, 2 H), 4.35(dt, 1 H), 4.27(s, 2 H), 3.78(s, 3 H), 3.75(s, 3 H), 1.26(d, 6 H) |

The following alkylating agents (as listed in Table 4) employed for the synthesis of the above listed final compounds are not commercially available and were synthesized, according to the following Examples 4, 5, and 6.

TABLE 4

| Alkylating agent | structure |
|---|---|
| (K1) | 4-(bromomethyl)benzenesulfonamide |
| (K2) | furan-2-ylmethyl methanesulfonate |
| (K3) | 4-(bromomethyl)-1,2-dimethoxybenzene |
| (K4) | 4-(bromomethyl)-1-fluoro-2-methoxybenzene |
| (K5) | N-(3-(chloromethyl)phenyl)methanesulfonamide |

Example 4

Preparation of 4-bromomethyl-benzene-sulphonamide (K1)

Step 1: 4-hydroxymethyl-benzene-sulphonamide.

LiAlH$_4$ (235 mg, 6.2 mmoles) was suspended in dry THF (10 mL) under nitrogen atmosphere. The suspension was cooled to 0° C. and 4-sulphamoyl-benzoic acid (500 mg, 2.48 mmoles, as a suspension in 10 mL of dry THF) was added. The resulting mixture was then refluxed for 18 hours. The reaction was quenched by addition of 3N HCl at 0° C. The quenched mixture was extracted with AcOEt, the organic layer was dried over Na$_2$SO$_4$ and evaporated to dryness. The crude material was purified by flash chromatography (SiO$_2$, petroleum ether/AcOEt from 9/1 to 1/1) to yield the title compound in amount of 105 mg.

Step 2: 4-bromomethyl-benzene-sulphonamide 4-hydroxymethyl-benzene-sulphonamide (0.105 mg, 0.56 mmoles) was dissolved in DCM (5 mL). Polymer supported triphenylphosphine (294 mg, 2.4 mmoles/g, 1.12 mmoles) was added, and the mixture was stirred with a shaker at room temperature for 10 minutes. CBr$_4$ (557 mg, 1.68 mmoles) was then added, and stirring was continued for 3 hours. The supported reagent was removed by filtration, the solvent was evaporated, and the crude material was purified by flash chromatography (SiO$_2$, petroleum ether/AcOEt 9/1) to yield the title compound as a light-yellow solid (70 mg).

Alkylating agents K3 and K4 were synthesized as described in step 2 of this same Example 4, starting from the corresponding commercially available alcohol derivatives.

Example 5

Preparation of methanesulfonic acid furan-2-ylmethyl ester (K$_2$)

Furan-2-yl-methanol (0.477 mL, 5.5 mmoles) was dissolved in dry DCM (10 mL). The solution was cooled to 0° C., and triethylamine (1.16 mL, 8.25 mmoles) and methanesulphonyl chloride (0.554 mL, 7.15 mmoles) were added dropwise. The resulting mixture was stirred at room temperature for 3 hours. The suspended solid (triethylamine hydrochloride) was removed by filtration, the filtrate was evaporated to dryness, and the crude material was employed in the next step without purification.

Step 2: 4-Bromomethyl-3,5-dichloro-pyridine (3,5-dichloro-pyridin-4-yl)-methanol (918 mg, 5.15 mmol) was dissolved in dry DCM (25 mL). Triphenylphosphine (2.70 g, 10.3 mmoles) was added, and the mixture was stirred at room temperature for 10 minutes. The solution was then cooled to 0° C., and CBr$_4$ (5.12 g, 15.4 mmoles) was added. The mixture was stirred at room temperature for 30 minutes, then the solvent was evaporated, and the crude was purified by flash chromatography (SiO$_2$, petroleum ether/AcOEt 95/5) to yield 850 mg of the title compound.

Example 6

Preparation of N-(3-chloromethyl-phenyl)-methane-sulphonamide (K5)

Step 1: (3-Amino-phenyl)-methanol.

3-Amino benzoic acid (1.05 g, 7.65 mmoles) was dissolved in THF (30 mL) under nitrogen atmosphere. Borane (BH$_3$ 1M solution in THF, 24 ml, 24 mmoles) was added, and the resulting solution was stirred at room temperature for 20 hours. The reaction mixture was then poured into a saturated NH$_4$Cl solution (100 mL) and extracted with AcOEt (3×100 mL). The organic layer was dried over Na$_2$SO$_4$ and evaporated to dryness to yield 388 mg of the title compound, which was employed in the next step without further purification.

Step 2: N-(3-chloromethyl-phenyl)-methane-sulphonamide

A solution of (3-amino-phenyl)-methanol (388 mg, 3.15 mmoles), lithium chloride (270 mg, 6.3 mmoles) and 2,6-lutidine (0.821 mL, 6.93 mmoles) in DMF (10 mL) was cooled at 0° C. under nitrogen atmosphere. Methanesulphonylchloride (0.536 mL, 6.93 mmoles) was added dropwise, and the mixture was stirred at room temperature for 3 hours. Water (30 mL) was then added, and the mixture was extracted with AcOEt (3×40 mL). The organic layer was washed with brine, dried over Na$_2$SO$_4$ and evaporated to dryness. The crude material was purified by flash chromatography (SiO$_2$, petroleum ether/AcOEt from 10/0 to 8/2) to yield 330 mg of the title compound.

Example 7

4-{[(3,5-dichloro-pyridin-4-ylmethyl)-(3,4-dimethoxy-phenyl)-amino]-methyl}-benzoic Acid (C16)

Compound C11 (350 mg, 0.75 mmol) was dissolved in MeOH (14 mL). 1N KOH (3 mL, 3 mmoles) was added, and the mixture was refluxed for 1 hour. The solvent was evaporated, the residue was dissolved in water (15 mL) and treated with 3N HCl to pH=1. The solution was then extracted with AcOEt (3×40 mL), and the organic layer was dried over Na$_2$SO$_4$ and evaporated to dryness. The crude was purified by flash chromatography (SiO$_2$, AcOEt/petroleum ether from 1/1 to 1/0) to yield the title compound in amount of 230 mg.

TABLE 5

| Compound | R₁ | R₂ | $(CH_2)_n$ | A | Analytical characterization |
|---|---|---|---|---|---|
| C16 | OMe | OMe | n = 1 | 4-(HOOC)-C₆H₄-CH₂- (benzoic acid) | MS (ESI⁺) 447.1 (MH⁺) (¹H-NMR CDCl₃): 8.41(s, 2 H); 7.93(d, 2 H); 7.31(d, 2 H); 6.73(d, 1 H); 6.52(m, 2 H); 4.64(s, 2 H); 4.41(s, 2 H); 3.81(s, 3 H); 3.75(s, 3 H) |

Example 8

Preparation of Final Compounds (C) (Scheme)

Synthesis of (3,5-dichloro-pyridin-4-ylmethyl)-(3,4-dimethoxy-phenyl)-thiophen-3-ylmethyl-amine Intermediate B1 (200 mg, 0.64 mmoles) was dissolved in MeOH (10 mL). Molecular sieves (4A, 200 mg) were added, and then thiophen-3-carbaldehyde (0.056 mL, 0.64 mmoles) was added. The mixture was stirred at room temperature for 2 hours, then NaBH₃CN (121 mg, 1.9 mmoles) was added. AcOH was added dropwise to pH=5. After 48 hours, molecular sieves were removed by filtration, and water was added (20 mL). The mixture was extracted with AcOEt (3×50 mL), and the organic layer was washed with brine, dried over Na₂SO₄, and evaporated to dryness. The crude material was purified by flash chromatography (SiO₂, petroleum ether/AcOEt from 9/1 to 7/3) to yield the title compound in amount of 173 mg.

Compounds C17, C18 and C19 are prepared following the same synthetic procedure, employing intermediate B1 and appropriate aldehydes, using suitable reagents. In Table 6, the symbol * in the formulae for the group A indicates the position at which the group A is bonded to the remainder of the molecule.

TABLE 6

| Compound | R₁ | R₂ | $(CH_2)_n$ | A | Analytical characterization |
|---|---|---|---|---|---|
| C17 | OMe | OMe | n = 1 | thiophen-3-yl | MS (ESI⁺) 409.1 (MH⁺) (¹H-NMR CDCl₃): 8.42(s, 2 H); 7.12(m, 1 H); 6.86-6.78(m, 2 H); 6.75(d, 1 H); 6.59-6.52(m, 2 H); 4.58(s, 2 H); 4.51(s, 2 H); 3.81(s, 3 H); 3.78(s, 3 H) |
| C18 | OMe | OMe | n = 1 | benzo[b]thiophen-3-yl | MS (ESI⁺) 459.4 (MH⁺) (¹H-NMR CDCl₃): 8.44(s, 2 H); 7.71(d, 1 H); 7.62(d, 1 H); 7.28(dd, 1 H); 7.24(dd, 1 H); 7.06(s, 1 H); 6.75(d, 1 H); 6.60(m, 2 H); 4.65(s, 2 H); 4.60(s, 2 H); 3.80(s, 3 H); 3.77(s, 3 H) |
| C19 | OMe | OMe | n = 1 | 3-hydroxyphenyl | MS (ESI⁺) 419.1 (MH⁺) (¹H-NMR CDCl₃): 8.42 (s, 2 H), 7.08(dd, 1 H), 6.67-6.82 (m, 3 H), 6.59-6.68(m, 1 H), 6.46-6.57(m, 2 H), 4.64(s, 2 H), 4.34(s, 2 H), 3.78-3.85 (m, 3 H), 3.72-3.79(m, 3 H) |

Legend:
*NMR
s = singlet
d = doublet
t = triplet
q = quartet
dd = doublet of doublets
m = multiplet
br = broad
ESI = electrospray Pharmacological Activity

Example 9

In Vitro Determination of PDE4 Inhibitory Activity in the Cell Free Assay

The U937 human monocytic cell line was used as source of PDE4 enzyme. Cells were cultured, harvested and supernatant fraction prepared essentially as described in T. J. Torphy, et al., *J. Pharmacol. Exp. Ther.*, 1992; 263:1195-1205.

PDE4 activity was determined in cells supernatants by assaying cAMP disappearance from the incubation mixtures. 50 μl of cell supernatant were incubated at 30° C. for 30 minutes in a final volume of 200 μl in the presence of 1.6 μM cAMP with or without the test compound (50 μl).

The concentration of the test compounds ranged between $10^{-12}$ M and $10^{-6}$ M.

Reactions were stopped by heat inactivation (2.5 minutes at 100° C.), and residual cAMP was measured using an electrochemiluminescence (ECL)-based immunoassay.

The results are expressed as mean±95% confidence limits of the molar concentration of the test compound producing 50% inhibition of cAMP disappearance ($IC_{50}$). The compounds $C_1$-$C_{14}$ were tested and their values of $IC_{50}$ in the cell free assay turned out to be comprised between 27 and 807 nM.

Percentage of inhibition of PDE4 activity was calculated, assuming cAMP disappearance in the absence of inhibitors as 100% and cAMP disappearance in heat inactivated samples as 0%.

All the $IC_{50}$ values of the tested compounds, representative of the invention, were less than 0.2 microM.

Example 10

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolysaccharides (LPS)-induced tumour necrosis factor-alpha (TNF-α release in peripheral blood mononuclear cells (PBMCs), was performed according to the method described by A. Hatzelmann, et al., *J. Pharmacol. Exp. Ther.*, 2001; 297:267-279 and by R. Draheim, et al., *J. Pharmacol. Exp. Ther.*, 2004; 308:555-563.

Cryopreserved human PBMCs, (100 μl/well) were incubated in 96-well plates ($10^5$ cells/well), for 30 minutes, in the presence or absence (50 microl) of the test compounds whose concentrations ranged from $10^{-12}$ M to $10^{-6}$ M. Subsequently, LPS (3 ng/ml) was added.

After 18 hours incubation at 37° C. in a humidified incubator under an atmosphere of 95% air and 5% $CO_2$, culture medium was collected and TNF-α measured by ELISA. The results are expressed as mean±95% confidence limits of the molar concentration of the test compound producing 50% inhibition of LPS-induced TNF-α release ($IC_{50}$).

The effects of the tested compounds were calculated as percent inhibition of TNF-α release, assuming LPS-induced TNF-α production in the absence of inhibitor compound as 100% and basal TNF-α production of PBMCs in the absence of LPS as 0%.

| Compound | $IC_{50}$ cell free (nM) | $IC_{50}$ PBMCS (nM) |
|---|---|---|
| C1 | 81 | 661 |
| C3 | 140 | 184 |
| C4 | 60 | 198 |
| C9 | 66 | 47.8 |
| C10 | 38 | 38 |
| C12 | 54 | — |
| C13 | 97.1 | 9.85 |
| C14 | 27 | 117 |

Comparative Examples

Following the teachings of WO 2005/061458 and WO 2006/135828, a comparative molecule corresponding respectively to compound 1 described above, from which it differs only in the lack of a methylene bridge between the amino nitrogen and the aryl portion and a comparative molecule similar to compound 5 described above, from which it differs in the lack of a methylene bridge between the amino nitrogen and the ring portion, which is a cyclopropylmethyl moiety have been synthesized. Both compounds show values of $IC_{50}$ PBMCs higher than 1000 nM.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

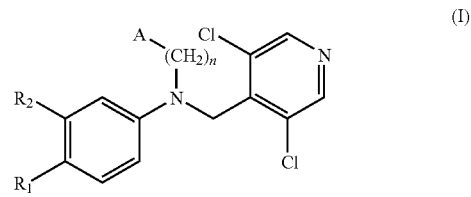

wherein:

n=1 or 2;

$R_1$ and $R_2$ are different or the same and are independently selected from the group consisting of $C_1$-$C_4$ alkyloxy, $C_3$-$C_7$ cycloalkyloxy, and ($C_3$-$C_7$)cycloalkyl-($C_1$-$C_3$)alkyloxy, provided at least one of $R_1$ and $R_2$ is $C_1$-$C_4$ alkyloxy, wherein in each of $R_1$ and $R_2$ one or more hydrogen atoms may be replaced with a halogen atom;

A is a group selected from the group consisting of phenyl, furyl, thiophenyl, and benzothiophenyl, each of which may be substituted with one or more substituents independently selected from the group consisting of:

OR$_3$, wherein R$_3$ is selected from the group consisting of
   H;
   C$_1$-C$_6$ alkyl; and
   C$_3$-C$_7$ cycloalkyl;
halogen;
CN;
HNSO$_2$R$_9$ wherein R$_9$ is C$_1$-C$_4$ alkyl;
SO$_2$R$_{10}$ wherein R$_{10}$ is C$_1$-C$_4$ alkyl, OH or NR$_6$R$_7$ wherein R$_6$ and R$_7$ are both H; and
COOR$_{13}$ wherein R$_{13}$ is H, C$_1$-C$_4$ alkyl, phenyl, or benzyl;
or a pharmaceutically acceptable salt thereof.

2. A compound or pharmaceutically acceptable salt thereof according to claim 1, wherein n is 1.

3. A compound or pharmaceutically acceptable salt thereof according to claim 1, wherein A is an unsubstituted phenyl group.

4. A compound or pharmaceutically acceptable salt thereof according to claim 1, wherein A is an optionally substituted phenyl group.

5. A compound or pharmaceutically acceptable salt thereof according to claim 1, wherein A is an unsubstituted furyl group.

6. A compound or pharmaceutically acceptable salt thereof according to claim 1, wherein A is an unsubstituted thiophenyl group.

7. A compound or pharmaceutically acceptable salt thereof according to claim 1, wherein R$_4$ and R$_5$ together with the nitrogen atom to which they are linked form a piperidyl ring.

8. A compound or pharmaceutically acceptable salt thereof according to claim 1, wherein A is an unsubstituted benzothiophenyl group.

9. A compound or pharmaceutically acceptable salt thereof according to claim 1, wherein A is furyl group or a benzothiophenyl group each of which may be substituted with one or more substituents selected from the group consisting of:
   OR$_3$, wherein R$_3$ is selected from the group consisting of
      H;
      C$_1$-C$_6$ alkyl; and
      C$_3$-C$_7$ cycloalkyl;
   halogen;
   CN;
   HNSO$_2$R$_9$ wherein R$_9$ is C$_1$-C$_4$ alkyl;
   SO$_2$R$_{10}$ wherein R$_{10}$ is C$_1$-C$_4$ alkyl, OH or NR$_6$R$_7$ wherein R$_6$ and R$_7$ are both H; and
   COOR$_{13}$ wherein R$_{13}$ is H, C$_1$-C$_4$ alkyl, phenyl, or benzyl.

10. A compound or pharmaceutically acceptable salt thereof, which is selected from the group consisting of:
   (3,5-dichloro-pyridin-4-ylmethyl)-(3,4-dimethoxy-phenyl)-(4-fluoro-benzyl)-amine;
   3-{[(3,5-dichloro-pyridin-4-ylmethyl)-(3,4-dimethoxy-phenyl)-amino]-methyl}-benzonitrile;
   (3,5-dichloro-pyridin-4-ylmethyl)-(3,4-dimethoxy-phenyl)-(3-methoxy-benzyl)-amine;
   (3,5-dichloro-pyridin-4-ylmethyl)-(3,4-dimethoxy-phenyl)-(4-methanesulfonyl-benzy)-amine;
   benzyl-(3,5-dichloro-pyridin-4-ylmethyl)-(3,4-dimethoxy-phenyl)-amine;
   (3,5-dichloro-pyridin-4-ylmethyl)-(3,4-dimethoxy-phenyl)-phenethyl-amine;
   (3,5-dichloro-pyridin-4-ylmethyl)-(3,4-dimethoxy-benzyl)-(3,4-dimethoxy-phenyl)-amine;
   (3,5-dichloro-pyridin-4-ylmethyl)-(3,4-dimethoxy-phenyl)-(3-fluoro-4-methoxy-benzyl)-amine;
   (3,5-dichloro-pyridin-4-ylmethyl)-(3,4-dimethoxy-phenyl)-furan-2-ylmethyl-amine;
   4-{[(3,5-dichloro-pyridin-4-ylmethyl)-(3,4-dimethoxy-phenyl)-amino]-methyl}-benzenesulfonamide 4-{[(3,5-dichloro-pyridin-4-ylmethyl)-(3,4-dimethoxy-phenyl)-amino]-methyl}-benzoic acid methyl ester;
   N-(3-{[(3,5-dichloro-pyridin-4-ylmethyl)-(3,4-dimethoxy-phenyl)-amino]-methyl}-phenyl)-methanesulfonamide;
   (3,5-dichloro-pyridin-4-ylmethyl)-(3,4-dimethoxy-phenyl)-(4-methoxy-benzyl)-amine;
   (3,5-dichloro-pyridin-4-ylmethyl)-(3-ethoxy-4-methoxy-phenyl)-(4-methoxy-benzyl)-amine;
   (3,5-dichloro-pyridin-4-ylmethyl)-(3-isopropoxy-4-methoxy-phenyl)-(4methoxy-benzyl)-amine;
   4-{[(3,5-dichloro-pyridin-4-ylmethyl)-(3,4-dimethoxy-phenyl)-amino]-methyl}-benzoic acid;
   (3,5-dichloro-pyridin-4-ylmethyl)-(3,4-dimethoxy-phenyl)-thiophen-2-ylmethyl-amine;
   benzo[1]thiophen-2-ylmethyl-(3,5-dichloro-pyridin-4-ylmethyl)-(3,4-dimethoxy-phenyl)-amine;
   3-{[(3,5-dichloro-pyridin-4-ylmethyl)-(3,4-dimethoxy-phenyl)-amino]-methyl}-phenol; and
   pharmaceutically acceptable salts thereof.

11. A compound or pharmaceutically acceptable salt thereof according to claim 10, which is (3,5-dichloro-pyridin-4-ylmethyl)-(3,4-dimethoxy-phenyl)-(4-fluoro-benzyl)-amine or a pharmaceutically acceptable salt thereof.

12. A compound or pharmaceutically acceptable salt thereof according to claim 10, which is (3,5-dichloro-pyridin-4-ylmethyl)-(3,4-dimethoxy-phenyl)-furan-2-ylmethyl-amine or a pharmaceutically acceptable salt thereof.

13. A compound or pharmaceutically acceptable salt thereof according to claim 10, which is (3,5-dichloro-pyridin-4-ylmethyl)-(3,4-dimethoxy-phenyl)-(4-methoxy-benzyl)-amine or a pharmaceutically acceptable salt thereof.

14. A pharmaceutical composition, comprising at least one compound or pharmaceutically acceptable salt thereof according to claim 1 and at least one pharmaceutically acceptable carrier and/or excipient.

15. A pharmaceutical composition, which comprises at least one pharmaceutically acceptable carrier and/or excipient and at least one compound or pharmaceutically acceptable salt thereof selected from the group consisting of:
   (3,5-dichloro-pyridin-4-ylmethyl)-(3,4-dimethoxy-phenyl)-(4-fluoro-benzyl)-amine;
   3-{[(3,5-dichloro-pyridin-4-ylmethyl)-(3,4-dimethoxy-phenyl)-amino]-methyl}-benzonitrile;
   (3,5-dichloro-pyridin-4-ylmethyl)-(3,4-dimethoxy-phenyl)-(3-methoxy-benzyl)-amine;
   (3,5-dichloro-pyridin-4-ylmethyl)-(3,4-dimethoxy-phenyl)-(4-methanesulfonyl-benzyl)-amine;
   benzyl-(3,5-dichloro-pyridin-4-ylmethyl)-(3,4-dimethoxy-phenyl)-amine;
   (3,5-dichloro-pyridin-4-ylmethyl)-(3,4-dimethoxy-phenyl)-phenethyl-amine;
   (3,5-dichloro-pyridin-4-ylmethyl)-(3,4-dimethoxy-benzyl)-(3,4-dimethoxy-phenyl)-amine;
   (3,5-dichloro-pyridin-4-ylmethyl)-(3,4-dimethoxy-phenyl)-(3-fluoro-4methoxy-benzy)-amine;
   (3,5-dichloro-pyridin-4-ylmethyl)-(3,4-dimethoxy-phenyl)-furan-2-ylmethyl-amine;
   4-{[(3,5-dichloro-pyridin-4-ylmethyl)-(3,4-dimethoxy-phenyl)-amino]methyl}-benzenesulfonamide 4-{[(3,5-dichloro-pyridin-4-ylmethyl)-(3,4-dimethoxy-phenyl)-amino]methyl}-benzoic acid methyl ester;
   N-(3-{[(3,5-dichloro-pyridin-4-ylmethyl)-(3,4-dimethoxy-phenyl)-amino]methyl}phenyl)-methanesulfonamide;

(3,5-dichloro-pyridin-4-ylmethyl)-(3,4-dimethoxy-phenyl)-(4-methoxy-benzyl)-amine;
(3,5-dichloro-pyridin-4-ylmethyl)-(3-ethoxy-4-methoxy-phenyl)-(4-methoxy-benzyl)-amine;
(3,5-dichloro-pyridin-4-ylmethyl)-(3-isopropoxy-4-methoxy-phenyl)-(4-methoxy-benzyl)-amine;
4-{[(3,5-dichloro-pyridin-4-ylmethyl)-(3,4-dimethoxy-phenyl)-amino]-methyl}-benzoic acid;
(3,5-dichloro-pyridin-4-ylmethyl)-(3,4-dimethoxy-phenyl)-thiophen-2-ylmethyl-amine;
benzo[b]thiophen-2-ylmethyl-(3,5-dichloro-pyridin-4-ylmethyl)-(3,4-dimethoxy-phenyl)-amine;
3-{[(3,5-dichloro-pyridin-4-ylmethyl)-(3,4-dimethoxy-phenyl)-amino]-methyl}-phenol; and
pharmaceutically acceptable salts thereof.

16. A pharmaceutical composition according to claim 15, which comprises (3,5-dichloro-pyridin-4-ylmethyl)-(3,4-dimethoxy-phenyl)-(4-fluoro-benzyl)-amine or a pharmaceutically acceptable salt thereof.

17. A pharmaceutical composition according to claim 15, which comprises (3,5-dichloro-pyridin-4-ylmethyl)-(3,4-dimethoxy-phenyl)-furan-2-ylmethyl-amine or a pharmaceutically acceptable salt thereof.

18. A pharmaceutical composition according to claim 15, which comprises (3,5-dichloro-pyridin-4-ylmethyl)-(3,4-dimethoxy-phenyl)-(4-methoxy-benzyl)-amine or a pharmaceutically acceptable salt thereof.

19. A method for the treatment of an inflammatory disease, disorder or condition characterized by or associated with an undesirable inflammatory immune response or induced by or associated with an excessive secretion of TNF-α and PDE4, said method comprising administering an effective amount of a compound or pharmaceutically acceptable salt thereof according to claim 1 to a subject in need thereof.

20. A method for the treatment of an inflammatory disease, disorder or condition characterized by or associated with an undesirable inflammatory immune response or induced by or associated with an excessive secretion of TNF-α and PDE4, said method comprising administering to a subject in need thereof an effective amount of at least one compound or pharmaceutically acceptable salt thereof selected from the group consisting of:
(3,5-dichloro-pyridin-4-ylmethyl)-(3,4-dimethoxy-phenyl)-(4-fluoro-benzyl)-amine;
3-{[(3,5-dichloro-pyridin-4-ylmethyl)-(3,4-dimethoxy-phenyl)-amino]methyl}-benzonitrile;
(3,5-dichloro-pyridin-4-ylmethyl)-(3,4-dimethoxy-phenyl)-(3-methoxy-benzyl)-amine;
(3,5-dichloro-pyridin-4-ylmethyl)-(3,4-dimethoxy-phenyl)-(4-methanesulfonyl-benzyl)-amine;
benzyl-(3,5-dichloro-pyridin-4-ylmethyl)-(3,4-dimethoxy-phenyl)-amine;
(3,5-dichloro-pyridin-4-ylmethyl)-(3,4-dimethoxy-phenyl)-phenethyl-amine;
(3,5-dichloro-pyridin-4-ylmethyl)-(3,4-dimethoxy-benzyl)-(3,4-dimethoxy-phenyl)-amine;
(3,5-dichloro-pyridin-4-ylmethyl)-(3,4-dimethoxy-phenyl)-(3-fluoro-4-methoxy-benzyl)-amine;
(3,5-dichloro-pyridin-4-ylmethyl)-(3,4-dimethoxy-phenyl)-furan-2-ylmethyl-amine;
4-{[(3,5-dichloro-pyridin-4-ylmethyl)-(3,4-dimethoxy-phenyl)-amino]methyl}-benzenesulfonamide 4-{[(3,5-dichloro-pyridin-4-ylmethyl)-(3,4-dimethoxy-phenyl)-amino]methyl}-benzoic acid methyl ester;
N-(3-{[(3,5-dichloro-pyridin-4-ylmethyl)-(3,4-dimethoxy-phenyl)-amino]-methyl}-phenyl)-methanesulfonamide;
(3,5-dichloro-pyridin-4-ylmethyl)-(3,4-dimethoxy-phenyl)-(4-methoxy-benzyl)-amine;
(3,5-dichloro-pyridin-4-ylmethyl)-(3-ethoxy-4-methoxy-phenyl)-(4-methoxy-benzyl)-amine;
(3,5-dichloro-pyridin-4-ylmethyl)-(3-isopropoxy-4-methoxy-phenyl)-(4-methoxy-benzy)-amine;
4-{[(3,5-dichloro-pyridin-4-ylmethyl)-(3,4-dimethoxy-phenyl)-amino]-methyl}-benzoic acid;
(3,5-dichloro-pyridin-4-ylmethyl)-(3,4-dimethoxy-phenyl)-thiophen-2-ylmethyl-amine;
benzo[b]thiophen-2-ylmethyl-(3,5-dichloro-pyridin-4-ylmethyl)-(3,4dimethoxy-phenyl)-amine;
3-{[(3,5-dichloro-pyridin-4-ylmethyl)-(3,4-dimethoxy-phenyl)-amino]methyl}-phenol; and
pharmaceutically acceptable salts thereof.

21. The method of claim 20, which comprises administering to said subject an effective amount of (3,5-dichloro-pyridin-4-ylmethyl)-(3,4-dimethoxy-phenyl)-(4-fluoro-benzyl)-amine or a pharmaceutically acceptable salt thereof.

22. The method of claim 20, which comprises administering to said subject an effective amount of (3,5-dichloro-pyridin-4-ylmethyl)-(3,4-dimethoxy-phenyl)-furan-2-ylmethyl-amine or a pharmaceutically acceptable salt thereof.

23. The method of claim 20, which comprises administering to said subject an effective amount of (3,5-dichloro-pyridin-4-ylmethyl)-(3,4-dimethoxy-phenyl)-(4-methoxy-benzyl)-amine or a pharmaceutically acceptable salt thereof.

24. A compound or pharmaceutically acceptable salt according to claim 1, wherein $R_1$ and $R_2$ are different or the same and are each $C_1$-$C_4$ alkyloxy.

* * * * *